US010884004B2

(12) United States Patent
Hirose et al.

(10) Patent No.: US 10,884,004 B2
(45) Date of Patent: Jan. 5, 2021

(54) TAGGABLE FLUORESCENT PROBE FOR CALCIUM ION DETECTION

(71) Applicant: The University of Tokyo, Tokyo (JP)

(72) Inventors: Kenzo Hirose, Tokyo (JP); Daisuke Asanuma, Tokyo (JP); Kohei Matsui, Tokyo (JP); Rieko Tanaka, Tokyo (JP)

(73) Assignee: The University of Tokyo, Tokyo (JP)

( * ) Notice: Subject to any disclaimer, the term of this patent is extended or adjusted under 35 U.S.C. 154(b) by 34 days.

(21) Appl. No.: 16/070,162

(22) PCT Filed: Jan. 13, 2017

(86) PCT No.: PCT/JP2017/001071
§ 371 (c)(1),
(2) Date: Nov. 13, 2018

(87) PCT Pub. No.: WO2017/122799
PCT Pub. Date: Jul. 20, 2017

(65) Prior Publication Data
US 2019/0094248 A1     Mar. 28, 2019

(30) Foreign Application Priority Data
Jan. 15, 2016   (JP) .................. 2016-006405

(51) Int. Cl.
*G01N 33/84*     (2006.01)
*C07D 493/10*    (2006.01)
*C09K 11/06*     (2006.01)
*G01N 33/58*     (2006.01)

(52) U.S. Cl.
CPC .......... *G01N 33/84* (2013.01); *C07D 493/10* (2013.01); *C09K 11/06* (2013.01); *G01N 33/582* (2013.01); *C09K 2211/1018* (2013.01)

(58) Field of Classification Search
CPC ............... C07D 493/10; C09K 11/06; C09K 2211/1018; G01N 33/582; G01N 33/84
See application file for complete search history.

(56) References Cited

U.S. PATENT DOCUMENTS

2013/0196362 A1    8/2013    Yang et al.

FOREIGN PATENT DOCUMENTS

JP          2015231364 A       12/2015
WO      WO 2015/153813 A1    10/2015

OTHER PUBLICATIONS

Yang et al. Functional analysis of G-protein coupled receptors using a new fluorescein lactone-based intracellular calcium indicator. Anal. Methods, 2010, vol. 2, pp. 295-298. (Year: 2010).*
Watkins et al. Fluorogenic affinity label for the facile, rapid imaging of proteins in live cells. Org. Biomol. Chem. 2009, vol. 7, pp. 3969-3975. (Year: 2009).*
Promega Technical Manual. Halotag technology: Focus on imaging. Promega Corporation, Madison, WI 53711-5399 USA, pp. 1-42. (Year: 2015).*
Li, D., et al., Genetic Targeting of a Small fluorescent Zinc Indicator to Cell Surface for Monitoring Zinc Secretion, ACS Chemical Biology, 10(4):1054-1063, Jan. 9, 2015.
Takahashi, A., Measurement of Intracellular Calcium, Physiol. Rev. 79:1089-1125, 1999.
Tsien, R.Y., et al., Calcium Homeostasis in Intact Lymphocytes: Cytoplasmic Free Calcium Monitored With a New, Intracellularly Trapped Fluorescent Indicator, J. Cell Biol. 94:325-334, 1982.
Zhao, M., et al. AM-Loading of Fluorescent Ca2+ Indicators Into Intact Single Fibers of Frog Muscle, Biophysical Journal, 72(6):2736-2747, Jun. 1997.

* cited by examiner

*Primary Examiner* — Shafiqul Haq
(74) *Attorney, Agent, or Firm* — Knobbe Martens Olson & Bear, LLP

(57) ABSTRACT

A fluorescent probe for calcium ion detection that has an excellent photofading resistance and quick $Ca^{2+}$ detection kinetics and can be localized at an arbitrary site in a cell is provided. The fluorescent probe contains a compound represented by the following general formula (I) or a salt thereof:

A method for detecting intracellular calcium ions including (a) introducing the compound above or a salt thereof into a cell and (b) measuring the fluorescence emitted by the compound or a salt thereof in the cell is also provided.

5 Claims, 5 Drawing Sheets

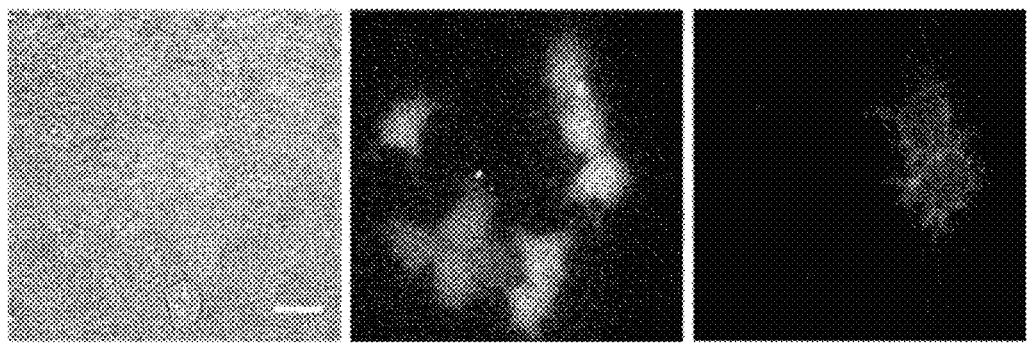

Co-staining with Calcium Green-1 and Halotag (registered trademark) TMR ligand (left: bright field, middle: Calcium Green-1, right: Halotag (registered trademark) TMR ligand). The scale bar is 20 μm.

B

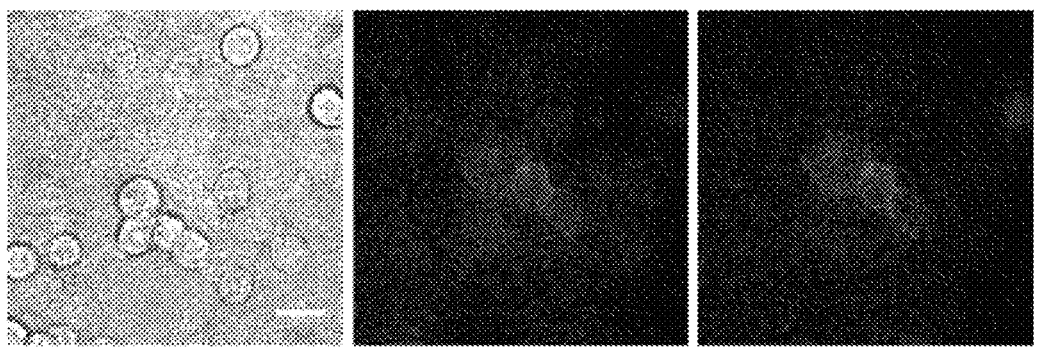

Co-staining with Compound 14 and Halotag (registered trademark) Oregon Green (registered trademark) ligand (left: bright field, middle: Compound 14, right: Halotag (registered trademark) Oregon Green (registered trademark) ligand). The scale bar is 20 μm.

Fig. 4
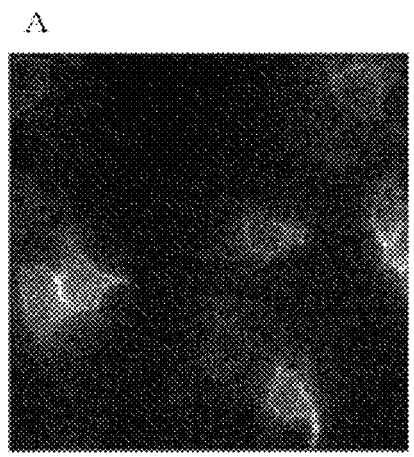
Labeling of HEK 293T/Halo-RimZF-CAAX
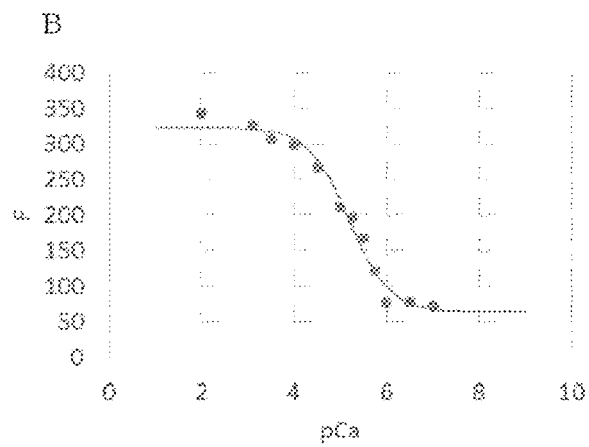
Curve fitting. The black circles (•) indicate each data point and showed a fit curve that is a curved line.

Fig. 5
A
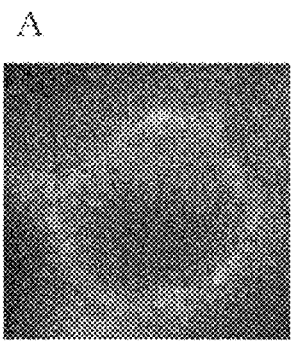
Labeling of HEK 293T/Halo-RimZF-CAAX
B
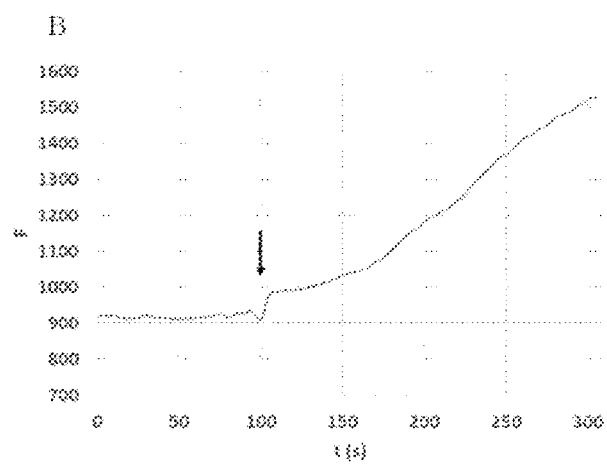
Changes in fluorescence intensity due to ionomycin stimulation.
The point of stimulation is indicated by a black arrow.

Fig. 6
A
Labeling of rat hippocampus-derived nerve cells expressing vglut1-chalo
B
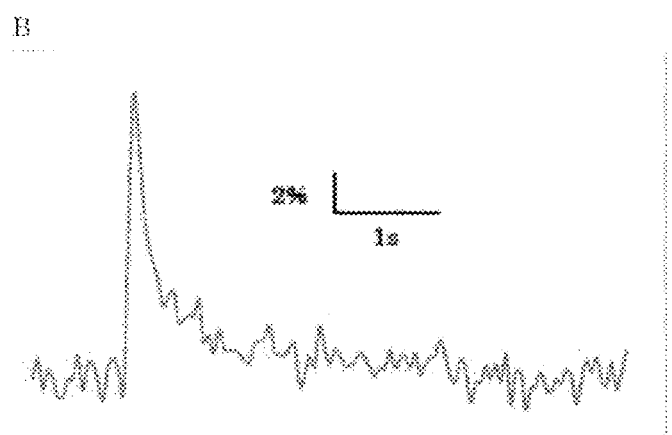
Changes in fluorescence intensity when applying electric stimulations (100 Hz, 10 times)

TAGGABLE FLUORESCENT PROBE FOR CALCIUM ION DETECTION

TECHNICAL FIELD

The present invention relates to a fluorescent probe for calcium ion detection that can be taggable in a cell.

BACKGROUND ART

Intracellular local $Ca^{2+}$ dynamics are known to be involved in the regulation of many cellular functions such as neurotransmitter release and mast cell degranulation. Since Roger Y. Tsien et al. developed quin 2 (Non-Patent Literature 1) in 1982, various $Ca^{2+}$ fluorescent probes such as fluo-3 and Calcium Green-1 have been developed and widely used for visualization of intracellular $Ca^{2+}$ dynamics (Non-Patent Literature 2).

Although these small molecule fluorescent probes have various features such as excellent photofading resistance and quick $Ca^{2+}$ detection kinetics, it is difficult to realize localization of such probes to any intracellular site, and it is extremely difficult to specifically visualize the intracellular local $Ca^{2+}$ dynamics.

CITATION LIST

Non-Patent Literature

Non-Patent Literature 1: Tsien, R. Y. et al. Calcium homeostasis in intact lymphocytes: cytoplasmic free calcium monitored with a new, intracellularly trapped fluorescent indicator. J. Cell Biol. 94, 325-334 (1982)

Non-Patent Literature 2: Takahashi, A. et al. Measurement of intracellular calcium. Physiol. Rev. 79, 1089-1125 (1999)

SUMMARY OF INVENTION

Technical Problem to be Solved

The purpose of the present invention is to provide a fluorescent probe for calcium ion detection that has an excellent photofading resistance and quick $Ca^{2+}$ detection kinetics and can be localized at an arbitrary site in a cell, and such a fluorescent probe has not been achieved by the prior art.

Means for Solving Problem

As a result of intensive studies for the purpose of developing a labelable probe on a HaloTag protein or the like by introducing a label site such as a HaloTag binding site or a target-accumulating site into the molecule of a $Ca^{2+}$ fluorescent probe with a xanthene dye excellent in photostability as its mother nucleus, the present inventors have found that the above problems can be solved by introducing a HaloTag binding site or the like from a linking group such as an amino group directly bonded to xanthene, and completed the present invention.

That is, according to the present invention,

[1] A compound represented by the following general formula (I) or a salt thereof:

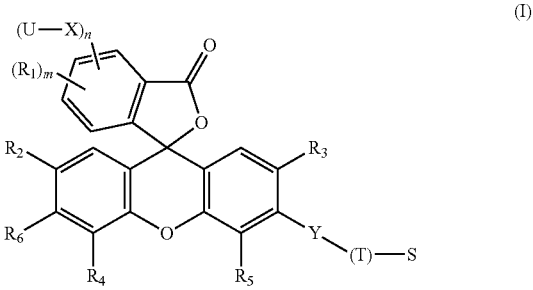

(wherein, $R_1$ at each occurrence represents a hydrogen atom or the same or different monovalent substituent on the benzene ring;

$R_2$ and $R_3$, each independently, represent a hydrogen atom, an alkyl group having 1 to 6 carbon atoms or a halogen atom;

$R_4$ and $R_5$ each independently, represent a hydrogen atom, an alkyl group having 1 to 6 carbon atoms or a halogen atom;

$R_6$ represents an acetoxy group, an acetoxymethoxy group, or a hydroxyl group;

X represents a linking group a between a benzene ring and U;

U represents a group capable of capturing calcium ions after hydrolysis;

Y represents a linking group b between a benzene ring and S;

T, if present, represents a cross-linking group;

S represents a label site;

m is an integer of 1 to 3, and n is an integer of 1 to 3, with the proviso that m+n=4).

[2] The compound according to [1] or a salt thereof, wherein the label site is a HaloTag ligand.

[3] The compound according to [1] or [2] or a salt thereof, wherein the group capable of capturing calcium ions after hydrolysis is selected from an ester compound of an aminophenol triacetic acid derivative and an ester compound of 1,2-bis(o-aminophenoxide) ethane-N,N,N',N'-tetraacetic acid derivative.

[4] The compound according to any one of [1] to [3] or a salt thereof, wherein X is an amide group.

[5] The compound according to any one of [1] to [4] or a salt thereof, wherein Y is an amino group or an amino group having one or two substituents.

[6] A compound represented by the following formula or a salt thereof.

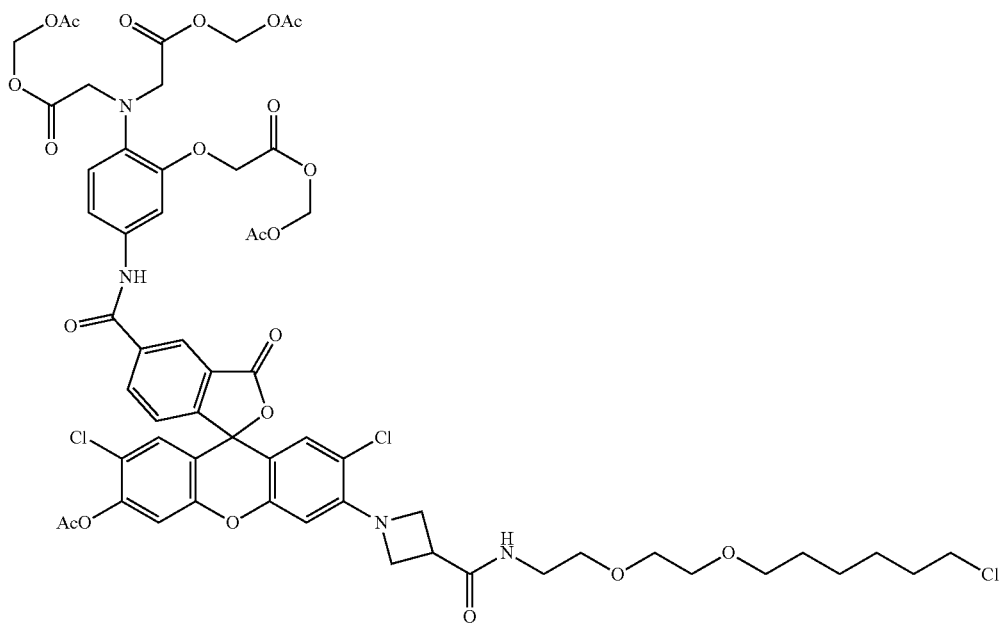 [SMILES: CC(=O)OCOC(=O)COc1cc(NC(=O)c2ccc3c(c2)C(=O)OC32c3cc(Cl)c(OC(C)=O)cc3Oc3cc(N4CC(C(=O)NCCOCCOCCCCCCCl)C4)c(Cl)cc32)ccc1N(CC(=O)OCOC(C)=O)CC(=O)OCOC(C)=O]

[7] A fluorescent probe including the compound according to any one of [1] to [6] or a salt thereof.

[8] A method for detecting intracellular calcium ions, comprising the steps of:

(a) introducing the compound according to anyone of [1] to [6] or a salt thereof into a cell, and (b) measuring the fluorescence emitted by the compound or a salt thereof in the cell.

Advantageous Effects of Invention

According to the present invention, by controlling the expression site of the HaloTag protein in the cell, it is possible to localize the fluorescent probe of the present invention at an arbitrary site in the cell and specifically detect a change in a local $Ca^{2+}$ concentration.

BRIEF DESCRIPTION OF DRAWINGS

FIG. 3 shows a selective labeling of HEK 293T/Halo-RimZF-CAAX with compound 14.

FIG. 4 shows the results of characterization of hCgapt3 localized in an HEK 293T cell membrane.

FIG. 5 shows the changes in fluorescence intensity of hCGapt3 by ionophore stimulation.

FIG. 6 shows the changes in fluorescence intensity with respect to electrical stimulation of hCGapt3 labeling vglut1-chalo expressed on nerve cells.

DETAILED DESCRIPTION OF THE PREFERRED EMBODIMENT

Figure 1:
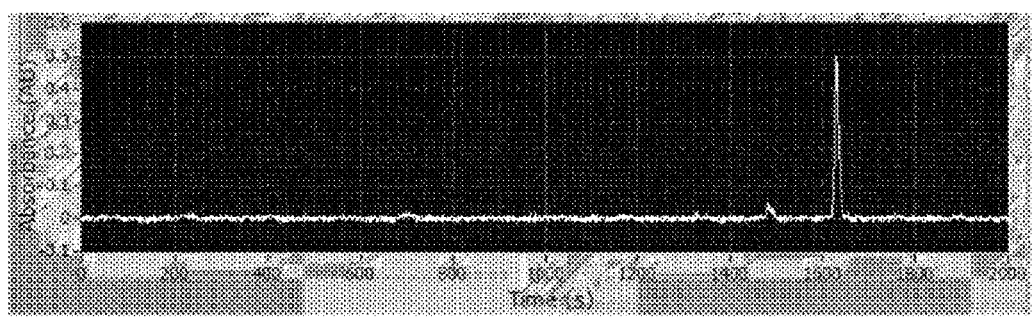
FIG. 1 shows an HPLC chromatogram of compound 14.

In the present specification, an "alkyl group" or the alkyl moiety of a substituent group including an alkyl moiety (such as an alkoxy group) refers, for example, to an alkyl group having about 1 to 6 carbon atoms, preferably about 1 to 4 carbon atoms, even more preferably about 1 to 3 carbon atoms, which is straight, branched, cyclic, or a combination thereof, unless otherwise mentioned. More specifically, examples of the alkyl group include methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, and the like.

In the present specification, the term "halogen atom" may be a fluorine atom, a chlorine atom, a bromine atom or an iodine atom, preferably a fluorine atom, a chlorine atom or a bromine atom.

One aspect of the present invention is a compound represented by the following general formula (I) or a salt thereof.

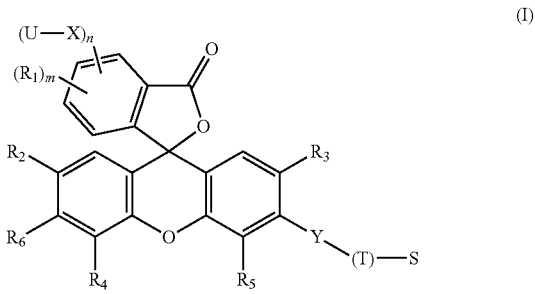

(I)

In the present invention, a label site such as a HaloTag binding site is introduced into the molecule of a $Ca^{2+}$ fluorescent probe having a xanthene dye as a mother nucleus. Here, if such a molecular design is inappropriate, $Ca^{2+}$ detection characteristics of probes and binding properties to HaloTag proteins change drastically, resulting in failure to realize desired functions. In the present invention, it is important to introduce a label site such as a HaloTag binding site at a specific position of the mother nucleus of a xanthene dye, and thereby it is possible to provide a fluorescent probe for calcium ion detection, which has an excellent photofading resistance and quick $Ca^{2+}$ detection kinetics and enables localization to any intracellular site.

In the general formula (I), $R_1$ at each occurrence represents a hydrogen atom or the same or different monovalent substituent on the benzene ring. Examples of the monovalent substituent include a halogen, an alkyl group which may be substituted, and the like.

m is an integer of 1 to 3, and the sum of m and n described later is 4.

When m is 2 or more, $R_1$ at each occurrence may be a hydrogen atom or the same or different monovalent substituent. In one preferred aspect of the present invention, when m is 2 or more, $R_1$ at each occurrence is all hydrogen.

In the general formula (I), $R_2$ and $R_3$ each independently represent a hydrogen atom, an alkyl group having 1 to 6 carbon atoms or a halogen atom.

When $R_2$ and $R_3$ each represent an alkyl group, one or two or more halogen atoms, carboxy groups, sulfonyl groups, hydroxyl groups, amino groups, alkoxy groups and the like may be present in the alkyl group, and the alkyl group represented by $R_2$ or $R_3$ may be a halogenated alkyl group, a hydroxyalkyl group, a carboxyalkyl group or the like. It is preferable that $R_2$ and $R_3$ are each independently a hydrogen atom or a halogen atom, and it is more preferable that both $R_2$ and $R_3$ are a fluorine atom or a chlorine atom.

$R_4$ and $R_5$ each independently represent a hydrogen atom, an alkyl group having 1 to 6 carbon atoms, or a halogen atom, and are the same as those described for $R_2$ and $R_3$. It is preferred that $R_4$ and $R_5$ are both hydrogen atoms.

$R_6$ represents an acetoxy group, an acetoxymethoxy group or a hydroxyl group, preferably an acetoxy group or an acetoxymethoxy group.

X represents a linking group a for introducing U, which will be described later, into the benzene ring. Examples of the linking group a include a carbonyl group, an alkylcarbonyl group, an ester group, an alkylester group, an amino group, an alkylamino group, an amide group, an isothiocyanate group, a sulfonyl chloride group, a haloalkyl group, a haloacetamide group, an azide group, an alkynyl group, and the like. In particular, a carbonyl group, an amide group, or an alkylcarbonyl group is preferable.

U represents a group capable of capturing calcium ions after hydrolysis. Examples of such a group capable of capturing calcium ions after hydrolysis include ester compounds of aminophenol triacetic acid derivatives and ester compounds of 1,2-bis(o-aminophenoxide) ethane-N,N,N', N'-tetraacetic acid derivatives, and acetoxymethyl ester compounds are particularly preferred.

Although not intending to be bound by any theory, hydrolysis is necessary for binding with $Ca^{2+}$, the hydrolysate is highly soluble in water and hardly enters the cell. Thus, it is preferable to use an ester derivative which can be introduced intracellularly in view of achieving application to cells. Then, it is thought that the ester which has entered the cell is hydrolyzed by an intracellular esterase and can bind to $Ca^{2+}$.

In the formula (I), the position on the benzene ring into which U—X— is introduced may be at any position, but it is preferably introduced at the 4-position with respect to the xanthene substitution position.

n is an integer of 1 to 3. When n is 2 or more, U—X— at each occurrence may be the same or different.

In the present invention, n is preferably 1 or 2, more preferably 1.

Y represents a linking group b for introducing S, which will be described later, into the benzene ring of xanthene. Examples of the linking group b include a carbonyl group, an alkylcarbonyl group, an ester group, an alkyl ester group, an amino group, an alkylamino group, an azetidine, an amide group, an isothiocyanate group, a sulfonyl chloride group, a haloalkyl group, a haloacetamide group, an azide group, an alkynyl group and the like, and particularly preferably a carbonyl group, an alkylcarbonyl group, an amino group, and azetidine.

T, when present, represents a crosslinking group and may be any crosslinking group as long as it functions as a spacer linking Y and S. Examples of the crosslinking group include, but not limited to, a substituted or unsubstituted hydrocarbon group (alkane, alkene, alkyne, cycloalkane, aromatic hydrocarbon, etc.), an ethylene glycol group, a diethylene glycol group, a triethylene glycol group, a polyethylene glycol group, an amide group, a carbonyl group, a heterocyclic group (such as a piperidinyl group), and the like. The crosslinking group may have a functional group capable of bonding to Y and S at one or both of its ends, and examples of such a functional group include an amino group, a carbonyl group, a carboxyl group, an amide group, and the like.

S represents a label site, examples of which include an N-hydroxysuccinimide ester, a HaloTag ligand (e.g. 2-(2-((6-chlorohexyl)oxy) ethoxy) ethaneamino group), a weakly basic amine, maleimide, an isothiocyanate group, a sulfonyl chloride group, a haloalkyl group, a haloacetamide group, an azide group, an alkynyl group, a benzylguanine derivative, a benzylcytosine derivative, and the like. The labeled portion of S also includes a polyethylene glycol group which may have a modifying group at one end or both ends, and examples of the modifying group include an amino group, a carbonyl group, a carboxyl group and the like. A non-limiting example of the polyethylene glycol group having a modifying group is 3-(2-(2-(2-aminoethoxy) ethoxy) ethoxy)propanoic acid.

In one preferred aspect of the present invention, S is a HaloTag ligand.

In the present invention, by introducing a label site such as a HaloTag ligand at a specific site on the benzene ring of xanthene, it becomes possible to control the expression site of the HaloTag protein or the like in the cell, resulting in the localization of the fluorescent probe of the present invention at a target site in the cell. Thereby, it is possible to specifically visualize the changes in the local $Ca^{2+}$ concentration.

One preferred aspect of the present invention is a compound represented by the following general formula (Ia) or a salt thereof.

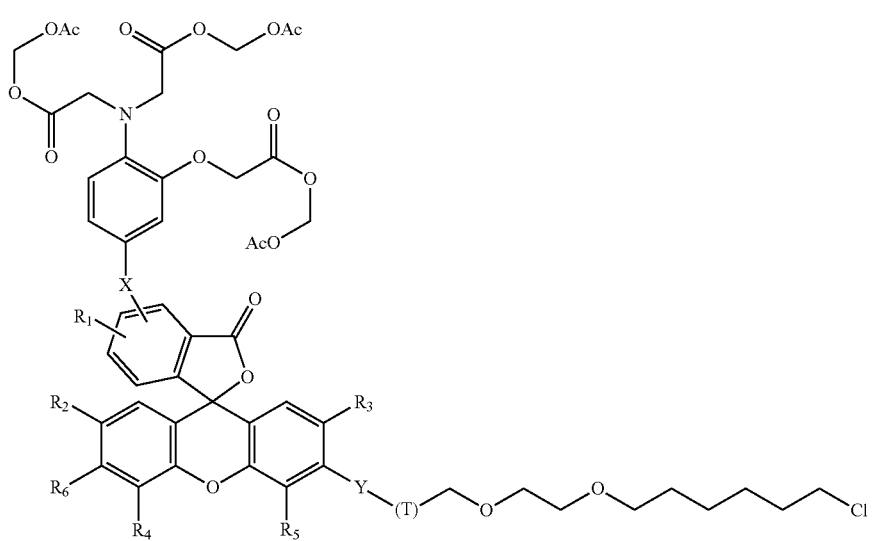

(Ia)

In the formula (Ia), $R_1$ to $R_6$, X, Y, and T are as defined in the general formula (I).

Also, one preferred aspect of the present invention is a compound represented by the following general formula (Ib) or a salt thereof.

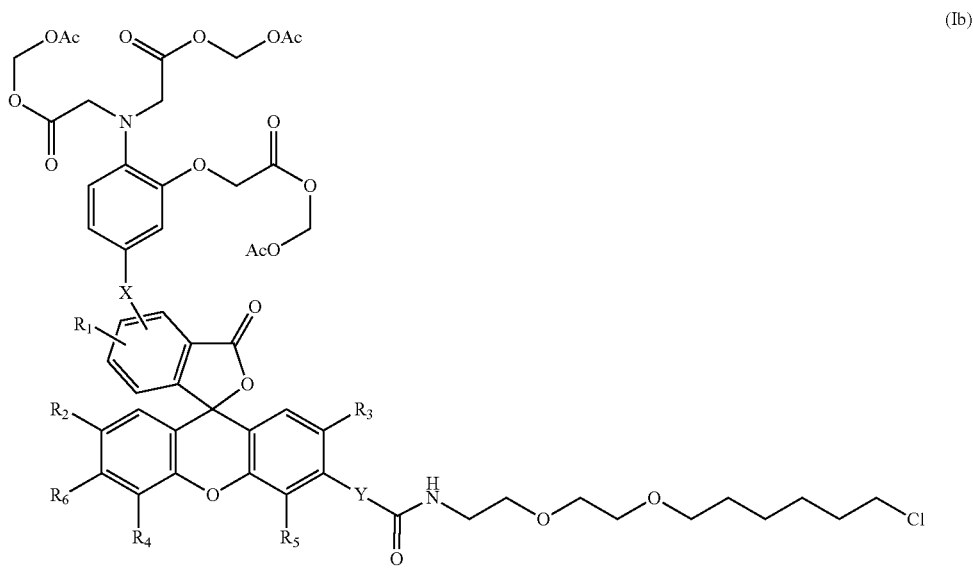

(Ib)

In the formula (Ib), $R_1$ to $R_6$, X, and Y are as defined in the general formula (I).

One preferred aspect of the present invention is a compound represented by the following formula or a salt thereof.

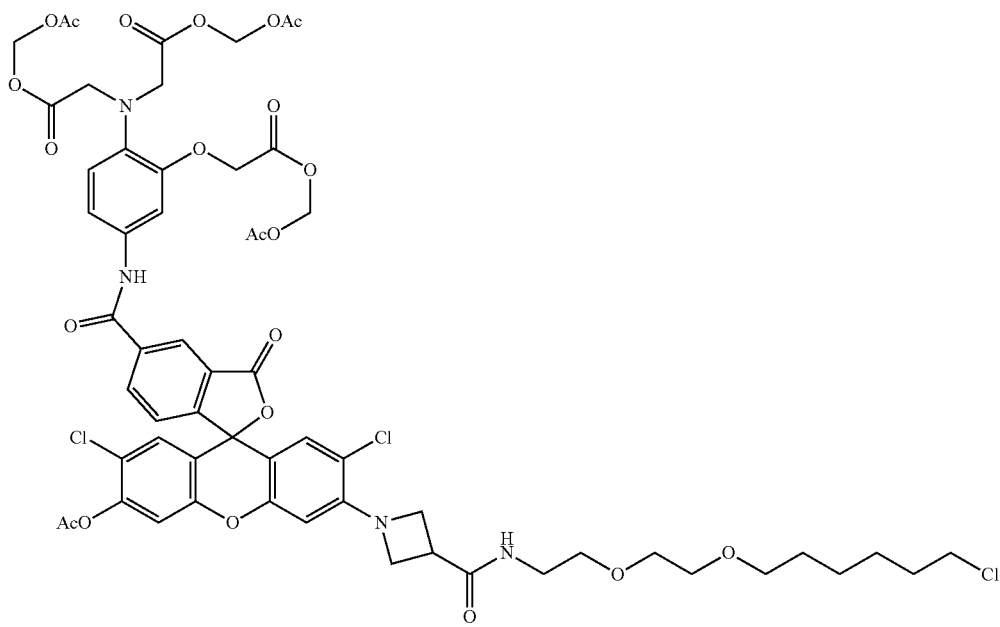 [SMILES: CC(=O)OCOC(=O)COc1cc(NC(=O)c2ccc3c(c2)C(=O)OC32c3cc(Cl)c(OC(C)=O)cc3Oc3cc(N4CC(C(=O)NCCOCCOCCCCCCCl)C4)c(Cl)cc32)ccc1N(CC(=O)OCOC(C)=O)CC(=O)OCOC(C)=O]

The compounds represented by the formulas (I), (Ia), and (Ib) according to the present invention can exist as acid addition salts or base addition salts. Examples of the acid addition salt include, for example, a mineral acid salt such as hydrochloride, sulfate, nitrate etc, or an organic acid salt such as methanesulfonate, p-toluenesulfonate, oxalate, citrate, tartrate etc. Examples of the base addition salt include metal salts such as sodium salt, potassium salt, calcium salt and magnesium salt, and organic amine salts such as ammonium salt and triethylamine salt. In addition to these, salts may be formed with amino acids such as glycine in some cases. The compound of the present invention or a salt thereof may exist as a hydrate or a solvate, and these substances are also within the scope of the present invention.

The compounds represented by the formulas (I), (Ia), and (Ib) of the present invention may have one or two or more asymmetric carbon atoms depending on the type of the substituents, but in addition to stereoisomers such as optically active substances based on one or two or more asymmetric carbons and diastereomers based on two or more asymmetric carbons, arbitrary mixtures of stereoisomers, racemates, and the like are included within the scope of the present invention.

Methods of preparing representative compounds among the compounds of the present invention are specifically illustrated in Examples herein. Therefore, those skilled in the art can appropriately select reaction raw materials, reaction conditions, reaction reagents and the like based on these descriptions, and modify or alter these methods as necessary to be able to obtain a compound represented by the general formulas (I), (Ia), and (Ib) according to the present invention.

The compounds represented by the formulae (I), (Ia), and (Ib) of the present invention are useful as a fluorescent probe for detecting calcium ions.

That is, another aspect of the present invention is a fluorescent probe including a compound represented by the formulae (I), (Ia), and (Ib) or a salt thereof.

Another aspect of the present invention is a method for detecting intracellular calcium ions, comprising the steps of (a) introducing a compound represented by the formula (I), (Ia) or (Ib) or a salt thereof into a cell, and (b) measuring the fluorescence emitted by the compound or a salt thereof in the cell.

The compound represented by the formulae (I), (Ia), and (Ib) or a salt thereof according to the present invention is substantially nonfluorescent or has only weak fluorescence in an environment free from calcium ions and has a characteristic of emitting strong fluorescence in an environment containing calcium ions. Accordingly, the compounds of the present invention represented by the formulae (I), (Ia), and (Ib) or salts thereof are extremely useful as calcium ion detection fluorescent probes for detecting $Ca^{2+}$ signals in cell membranes and synapses under physiological conditions.

The method of using the fluorescent probe of the present invention is not particularly limited, and the fluorescent probe of the present invention can be used in the same manner as conventionally known fluorescent probes. In general, the compound of the present invention represented by the formulae (I), (Ia), and (Ib) or a salt thereof is dissolved in an aqueous medium such as physiological saline and a buffer solution, or a mixture of an aqueous medium and a water-miscible organic solvent such as ethanol, acetone, ethylene glycol, dimethyl sulfoxide, and dimethylformamide, and this solution is added to an appropriate buffer containing cells or tissues. Then, the fluorescence spectrum may be measured. The fluorescent probe of the present invention may be used in the form of a composition in combination with suitable additives. For example, the fluorescent probe can be combined with additives such as buffering agents, solubilizing agents, pH adjusting agents and the like.

EXAMPLES

Hereinafter, the present invention will be described by way of Examples, but the present invention is not limited thereto.

Example 1

Synthesis of bis(acetoxymethyl) 2,2'-((4-(3'-acetoxy-2',7'-dichloro-6'-(3-((2-(2-((6-chloro hexyl)oxy)ethoxy)ethyl)carbamoyl)azetidin-1-yl)-3-oxo-3H-spiro[isobenzofuran-1,9'-xanthene]-5-carboxylic acid amido)-2-(2-(acetoxymethoxy)-2-oxoethoxy)phenyl)azanediyl) diacetate (Compound 14)

Compound 14, one of the compounds of the present invention, was synthesized according to the procedure of the following reaction scheme.

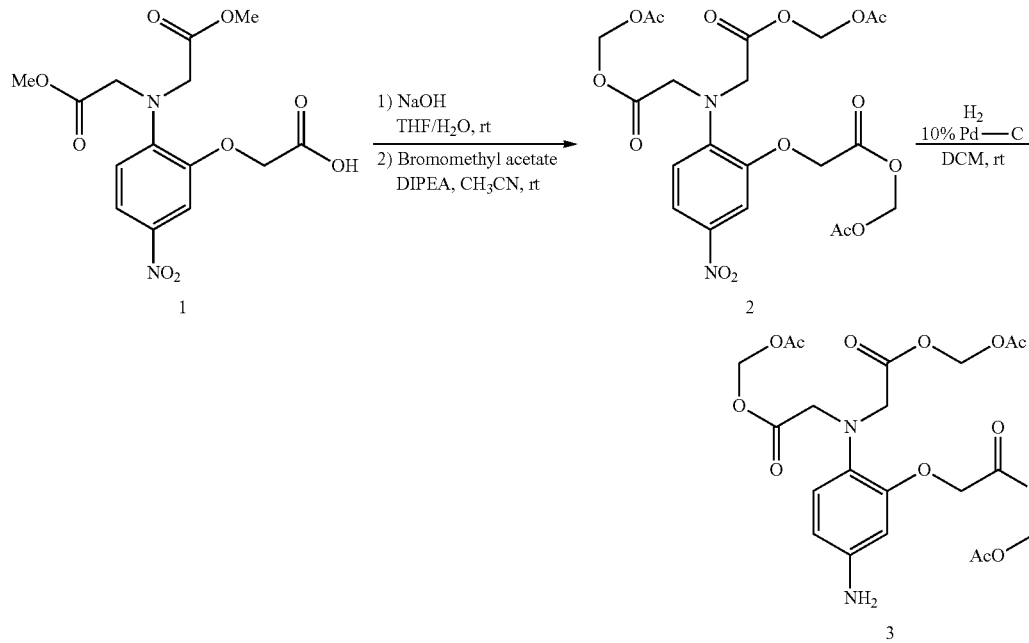

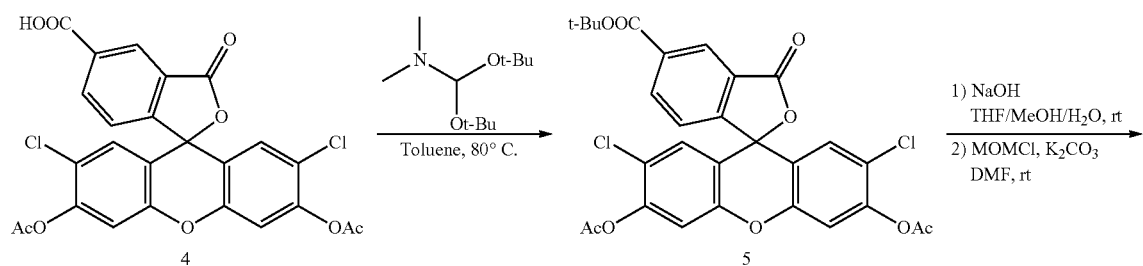

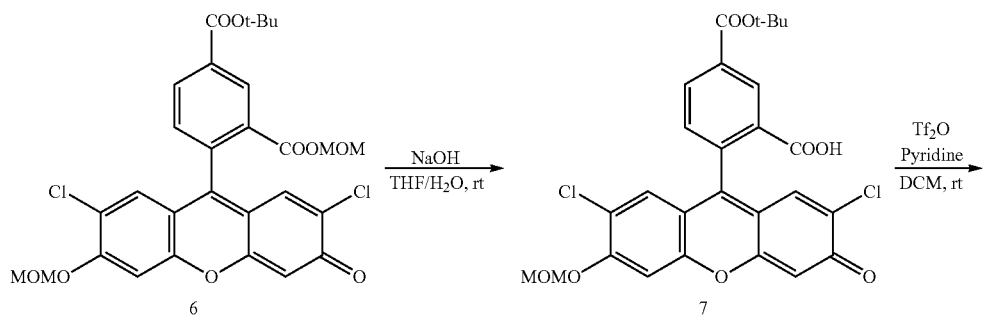

-continued
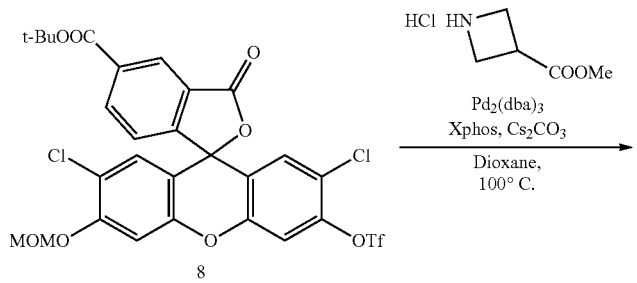
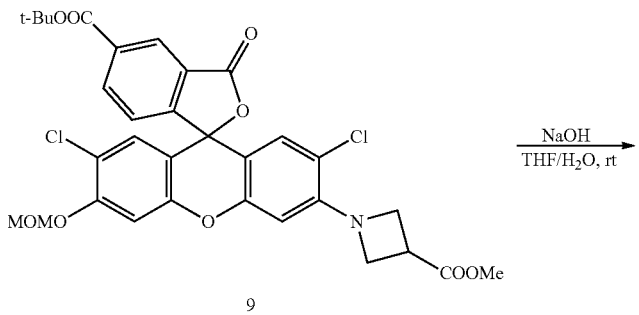
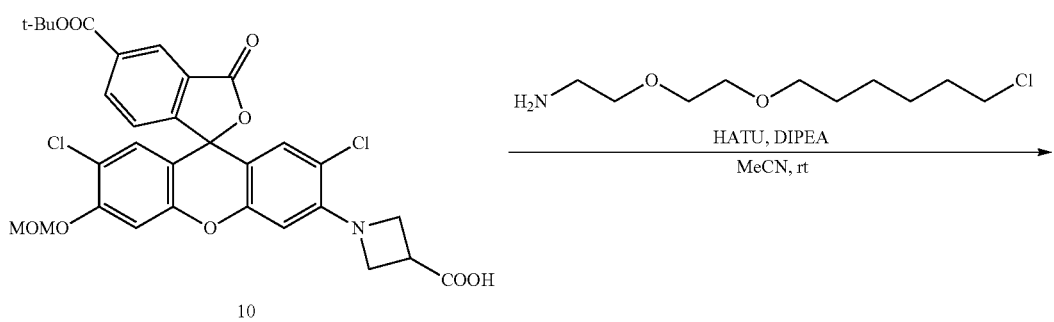
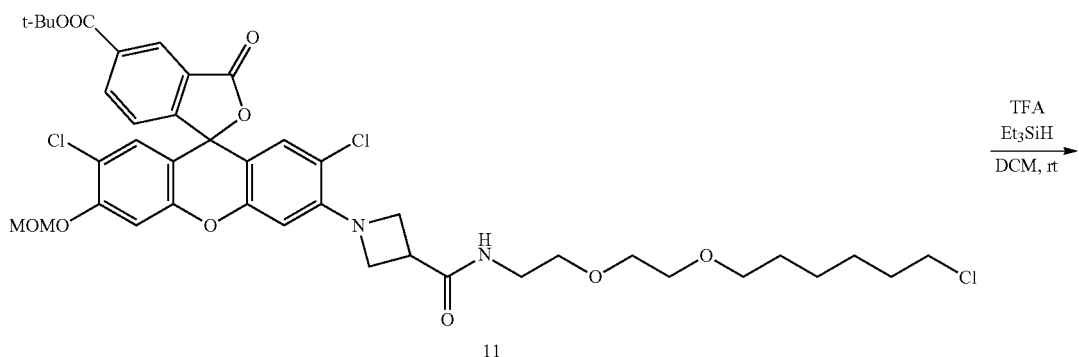
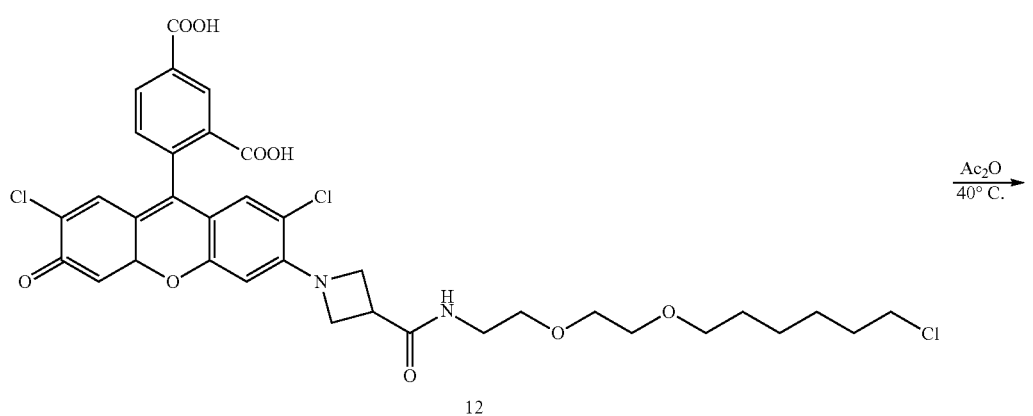

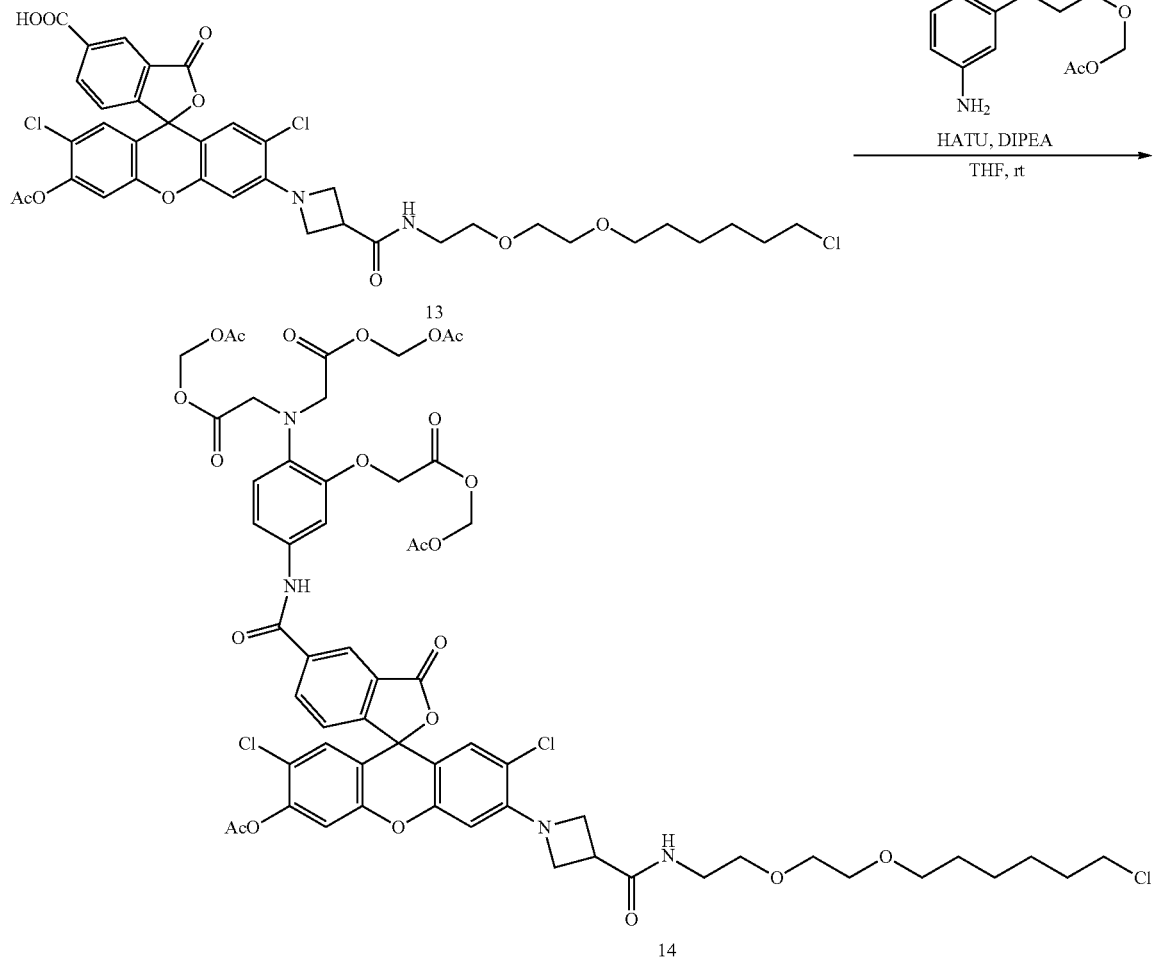

(1) Synthesis of bis(acetoxymethyl)2,2'-((2-(2-(acetoxymethoxy)-2-oxoethoxy)-4-aminophenyl)azanediyl)diacetate (Compound 3)

2-(2-(Bis(2-methoxy-2-oxoethyl)amino)-5-nitrophenoxy) acetic acid (Compound 1) (767.8 mg, 2.155 mmol) was placed in a flask and dissolved in THF (15 mL). After addition of 1N NaOH (6.7 mL) while stirring the solution, the mixture was stirred at room temperature under light-shielding conditions for 40 minutes. Then, 1N NaOH (2.1 mL) was added, and the mixture was further stirred for 30 minutes. Ethyl acetate was added to the solution, and the mixture was extracted with water. 1N HCl (15 mL) was added to the resulting solution and extracted with ethyl acetate (2 times). The crude product thus obtained was dried over anhydrous Na$_2$SO$_4$, dried in vacuo and then dissolved in acetonitrile (30 mL). DIPEA (4.8 mL) and methyl bromoacetate (1.25 mL) were added to the solution with stirring, and the mixture was shielded from light and stirred overnight at room temperature. After addition of water, the reaction mixture was extracted with DCM.

The resulting crude product was dried over anhydrous Na$_2$SO$_4$ and the solution was concentrated. The residue was purified by silica gel column chromatography (elution solvent: AcOEt/Hexane=1/1) to give 702.0 mg of bis(acetoxymethyl) 2,2'-((2-(2-(acetoxymethoxy)-2-oxoethoxy)-4-nitrophenyl) azanediyl)diacetate (Compound 2). This compound 2 was dissolved in dry DCM (20 mL), mixed with 10% palladium carbon (two spatulas), then shielded from light and stirred overnight at room temperature under a hydrogen atmosphere. Hydrogen was further introduced to the reaction mixture, and the mixture was shielded from light and stirred at room temperature for 4 hours. After addition of 10% palladium on carbon (two spatulas), the mixture was further stirred overnight. The reaction mixture was filtered to remove palladium carbon and the solution was concentrated. Purification by silica gel column chromatography (elution solvent: AcOEt/Hexane=3/1) gave 41.9 mg of compound 3 (3-step yield: 180).

$^1$HNMR (400 MHz, CDCl$_3$): δ/ppm, 6.86 (d, 1H, J=8.4 Hz), 6.26-6.28 (m, 1H), 6.2 (d, 1H, J=2.4 Hz), 5.81 (s, 2H), 5.74 (s, 4H), 4.70 (s, 2H), 4.13 (s, 4H), 2.11 (s, 3H), 2.09 (s, 6H)

¹³CNMR (100 MHz, CDCl₃): δ/ppm, 170.22, 169.69, 169.63, 168.06, 151. 73, 143.51, 130.71, 123.44, 109.27, 103.41, 79.41, 79.29, 77.48, 76. 84, 66.05, 54.04, 20.79, 20.73

HRMS (ESI⁺): Calcd. for [M+H]⁺ 515.15131; Found 515.15199; Δ=0.00068.

(2) Synthesis of 1-(tert-butyl) 3-(methoxymethyl) 4-(2,7-dichloro-6-(methoxymethoxy)-3-oxo-3H-xanthen-9-yl)isophthalate (Compound 6)

3',6'-Diacetoxy-2',7'-dichloro-3-oxo-3H-spiro[isobenzofuran-1,9'-xanthene]-5-carboxylic acid (Compound 4) (1.0034 g, 1.8958 mmol) was placed in a flask, dissolved in dry toluene (6 mL) and warmed to 80° C. with stirring. The solution was kept at the same temperature for 10 minutes and then N,N-dimethylformamide di-tert-butyl acetal (2.7 mL) was added dropwise. The mixture was further stirred for 10 minutes and then the temperature was lowered to room temperature. NaHCO₃ was added to the reaction mixture and extracted with DCM (2 times). The crude product thus obtained was dried over anhydrous Na₂SO₄ and dried in vacuo. The residue was purified by silica gel column chromatography (elution solvent: AcOEt/Hexane=1/2) to give 774 mg of 5-(tert-butoxycarbonyl)-2',7'-dichloro-3-oxo-3H-spiro[isobenzofuran-1,9'-xanthene]-3',6'-diyldiacetate (Compound 5) as an orange solid.

The obtained Compound 5 (774 mg, 1.32 mmol) was placed in a flask, and a mixed solution (20 mL) of THF:MeOH=1:1 was added. 1M NaOH (3 mL) was added thereto with stirring, and the mixture was stirred at room temperature under light-shielding conditions for 2 hours. 1N HCl (3 mL) and water were added to the reaction mixture, and the mixture was extracted with ethyl acetate. The ethyl acetate solution of the resulting crude product was dried over anhydrous Na₂SO₄ and dried in vacuo. The residue was dissolved in dry DMF (15 mL), potassium carbonate (457 mg, 3.31 mmol) was added, and the solution was cooled to 0° C. Chloromethyl methyl ether (301 µL, 3.97 mmol) was added dropwise slowly (about 10 minutes) with stirring at the same temperature, then the solution was allowed to warm to room temperature and stirred overnight. Ethyl acetate (10 mL) and NH₄Cl (10 mL) were added to the reaction mixture, water was then added, and the resulting mixture was extracted with ethyl acetate (twice). The crude product thus obtained was washed with brine, dried over anhydrous Na₂SO₄ and dried in vacuo. The residue was purified by silica gel column chromatography (elution solvent: AcOEt/Hexane=1/2) to obtain 552 mg of compound 6 as an orange solid (3-step yield: 490).

¹HNMR (400 MHz, CDCl₃): δ/ppm, 8.93 (d, 1H, J=3.2 Hz), 8.44 (dd, 1H, J=8.0, 1.6 Hz), 7.54 (d, 1H, J=8.0 Hz), 7.37 (s, 1H), 7.01 (s, 1H), 6.96 (s, 1H), 6.49 (s, 1H), 5.42 (s, 2H), 5.25-5.31 (m, 2H), 3.55 (s, 3H), 3.36 (s, 3H), 1.70 (s, 9H)

¹³CNMR (100 MHz, CDCl₃): δ/ppm, 177.24, 163.69, 163.58, 157.45, 156.86, 151.88, 148.18, 137.23, 135.31, 134.01, 133.78, 132.26, 130.82, 130.05, 127.55, 126.77, 120.67, 117.57, 115.13, 105.47, 103.38, 95. 13, 91.60, 82.39, 57.63, 56.64, 27.93

HRMS (ESI⁺): Calcd. for [M+H]⁺ 589.10321; Found 589.10266; Δ=0.00055.

(3) Synthesis of (tert-butyl 2',7'-dichloro-3'-(methoxymethoxy)-3-oxo-6'-((trifluoromethyl)sulfonyl)oxy)-3H-spiro[isobenzofuran-1,9'-xanthene]-5-carboxylate salt) (Compound 8)

Compound 6 (254.5 mg, 0.43178 mmol) was placed in a flask and dissolved in dry THF (5 mL). Water (2 mL) and 1N NaOH (1.55 mL) were added to the solution while stirring the solution, and the resulting mixture was stirred at room temperature for 80 minutes. 1N HCl (2 mL) and water were added to the reaction mixture and extracted with DCM. The resulting crude product was dried over anhydrous Na₂SO₄ and dried in vacuo. The residue was purified by silica gel column chromatography (elution solvent: AcOEt/Hexane=1/1) to obtain 219 mg of an orange solid. The compound (219 mg) thus obtained was placed in a flask and dissolved in dry DCM (10 mL). The solution was cooled to 0° C., pyridine (324.1 µL, 4.0157 mmol) was slowly added (over a period of about 10 minutes) with stirring, and trifluoromethanesulfonic anhydride (202.3 µL, 1.2047 mmol) was dropwise added slowly (over a period of about 10 minutes). Thereafter, the solution was warmed to room temperature and stirred overnight at room temperature under light-shielding conditions. Water was added to the reaction mixture, and the mixture was extracted with DCM. Then, the extracted solution was washed with 1N HCl. The crude product so obtained was dried over anhydrous Na₂SO₄ and the solvent was evaporated. The residue was purified by silica gel column chromatography (elution solvent: AcOEt/Hexane=1/2) to obtain 243 mg of compound 8 as a filmy white solid (2-step yield: 83.1%).

¹HNMR (400 MHz, CDCl₃): δ/ppm, 8.68 (dd, 1H, J=1.2, 0.8 Hz), 8.38 (dd, 1H, J=8.0, 1.2 Hz), 7.36 (s, 1H), 7.25-7.28 (1H), 7.18 (s, 1H), 6.94 (s, 1 H), 6.78 (s, 1H), 5.30-5.34 (m, 2H), 3.53 (s, 3H), 1.59-1.70 (9H)

¹³CNMR (100 MHz, CDCl₃): δ/ppm, 167.71, 163.73, 155.00, 154.93, 150. 07, 149.94, 146.39, 136.91, 135.27, 128.64, 127.21, 126.21, 123.96, 122.36, 120.31, 120.27, 119.92, 112.53, 104.33, 95.26, 82.83, 80.55, 77.48, 76.84, 56.73, 28.13

HRMS (ESI⁺): Calcd. for [M+H]⁺ 677.02628; Found 677.02655; Δ=0.00027.

(4) Synthesis of tert-butyl 2',7'-dichloro-3'-(3-((2-(2-((6-chlorohexyl)oxy)ethoxy)ethyl)carbamoyl)azetidin-1-yl)-6'-(methoxymethoxy)-3-oxo-3H-spiro[isobenzofuran-1,9'-xanthene]-5-carboxylate (Compound 11)

Compound 8 (300.8 mg, 0.4440 mmol) was added to a flask and dissolved in dioxane (18 mL), then methyl azetidine-3-ester hydrochloride (101.0 mg, 0.6661 mmol), 2-dicyclohexylphosphino-2',4',6'-triisopropylbiphenyl-1,1'-biphenyl (Xphos; 106.0 mg, 0.2220 mmol), tris(dibenzylideneacetone)dipalladium (0) (Pd₂(dba)₃; 81.3 mg, 0.0888 mmol) and cesium carbonate (723.4 mg, 2.220 mmol) were added thereto. The reaction solution was heated to 100° C. under an argon atmosphere and stirred for 6 hours. The insoluble solid in the solution was filtered through celite and the solution was concentrated. The crude product was purified by silica gel column chromatography (elution solvent: AcOEt/Hexane=1/2) to obtain 76.8 mg of methyl 1-(5-(tert-butoxycarbonyl)-2',7'-dichloro-3'-(methoxymethoxy)-3-oxo-3H-spiro[isobenzofuran-1,9'-xanthen]-6'-yl) azetidine-3-carboxylate (Compound 9) as a colorless transparent liquid.

HRMS (ESI⁺): Calcd. for [M+H]⁺ 642.12976; Found 642.12976; Δ=0.0.

Compound 9 (76.8 mg, 0.120 mmol) thus obtained was dissolved in dry THF (5 mL), water (5 mL) was added, and then 143 µL of 1N NaOH was added with stirring. The reaction mixture was stirred at room temperature for 1 hour, 160 µL of 1N HCl was added, then water was added thereto. The mixture was extracted with ethyl acetate. After that, the extract was dried over anhydrous $Na_2SO_4$ and the solvent was evaporated. The crude product was purified by silica gel column chromatography (elution solvent: DCM/MeOH=94/6) to obtain 67.5 mg of 1-(5-(tert-butoxycarbonyl)-2',7'-dichloro-3'-(methoxymethoxy)-3-oxo-3H-spiro[isobenzofuran-1,9'-xanthen]-6'-yl) azetidine-3-carboxylic acid (Compound 10).

HRMS (ESI$^+$): Calcd. for [M+H]$^+$ 628.11411; Found 628.11410; Δ=0.00001.

The obtained Compound 10 (67.5 mg, 0.107 mmol) was added to a flask and dissolved in acetonitrile (7 mL). While stirring the solution, 129 μL of 1M 2-(2-((6-chlorohexyl)oxy)ethoxy)ethane-1-amine dissolved in acetonitrile was added and O-(benzotriazol-1-yl)-N, N, N',N'-tetramethyluronium hexafluorophosphate (HATU) (49 mg, 0.13 mmol) and N,N-dimethylethylenediamine (DIPEA) (93.5 μL, 0.537 mmol) were further added. Then, the mixture was stirred at room temperature for 1 hour. After distilling off the solvent, the residue was purified by silica gel column chromatography (elution solvent: AcOEt/Hexane=2/1) to obtain 52.2 mg of compound 11 as a colorless clear liquid (3-step yield: 14%).

$^1$HNMR (400 MHz, CDCl$_3$): δ/ppm, 8.627-8.632 (m, 1H), 8.34 (dd, 1H, J=8. 0, 1.6 Hz), 7.21-7.24 (m, 1H), 7.10 (s, 1H), 6.70 (s, 1H), 6.53 (s, 1H), 6.33 (s, 1H), 5.30 (q, 2H, J=10.8, 6.8 Hz), 4.21-4.33 (m, 4H), 3.45-3.63 (m, 16H), 1.35-1.81 (m, 17H) $^{13}$CNMR (100 MHz,): δ/ppm, 171.50, 168.3 7, 164.03, 155.64, 154.48, 150.72, 150.59, 149.26, 136.43, 134.61, 1 29.41, 128.72, 126.84, 126.77, 124.07, 118.99, 115.96, 112.33, 108. 81, 104.27, 101.47, 95.17, 82.53, 82.51, 71.34, 70.33, 70.09, 69.66, 56.64, 56.00, 45.11, 39.49, 34.97, 32.57, 29.52, 28.25, 26.73, 25.47 HRMS (ESI$^+$): Calcd. for [M+H]$^+$ 833.23745; Found 833.23521; Δ=0.00234.

(5) Synthesis of Compound 14

Compound 11 (30.5 mg, 0.0366 mmol) was added to a flask and dissolved in dry DCM (10 mL). Triethylsilane (17.5 μL, 0.110 mmol) and TFA (1 mL) were added while stirring the solution, and the mixture was stirred overnight at room temperature. Toluene was then added to the reaction mixture, distilled off and azeotroped with methanol. The residue was redissolved in DMF (1.5 mL), and HPLC (ODS, A (water and 0.1% TFA): B (acetonitrile and 0.1% TFA)=99:1 to 1:99, 20 min) was performed. The purified solution was transferred to a 30 mL vial and dried in vacuo to obtain 21.4 mg of 4-(2,7-dichloro-6-(3-((2-(2-((6-chlorohexyl)oxy) ethoxy)ethyl) carbamoyl) azetidin-1-yl)-3-oxo-3H-xanthen-9-yl)isophthalic acid (Compound 12).

HRMS (ESI$^+$): Calcd. for [M+H]$^+$ 733.14864; Found 733.14922; Δ=0.00058.

Compound 12 (21.4 mg, 0.0292 mmol) thus obtained was dissolved in dry THF (1 mL), acetic anhydride (0.5 mL) was added while stirring the solution, and the mixture was warmed to 40° C., then stirred for 2 and a half hours. After that, the reaction mixture was distilled off and purified twice by silica gel column chromatography (elution solvent: first time, DCM/MeOH=95/5, second time, DCM/MeOH=97/3) to obtain 6.5 mg of 3'-acetoxy-2',7'-dichloro-6'-(3-((2-(2-((6-chlorohexyl)oxy) ethoxy)ethyl) carbamoyl) azetidin-1-yl)-3-oxo-3H-spiro[isobenzofuran-1,9'-xanthene]-5-carboxylic acid (Compound 13) as a pale pink clear liquid.

HRMS (ESI$^+$): Calcd. for [M+H]$^+$ 775.15920; Found 775.15964; Δ=0.00044.

The obtained Compound 13 (6.5 mg, 0.084 mmol) was added to a 30 mL vial and dissolved in acetonitrile (1 mL). While stirring the solution, a 1M acetonitrile solution (83.8 μL, 0.00838 mmol) in which the Compound 13 was dissolved was added. HATU (3.8 mg, 0.010 mmol) and DIPEA (7.3 μL, 0.042 mmol) were added to the resulting reaction mixture, and the mixture was stirred for 3 hours. After distilling off the reaction mixture, the residue was purified by PLC (developing solvent; DCM:MeOH=93:7) to obtain 9.9 mg of compound 14 as a pale pink liquid (3-step yield: 14%).

$^1$HNMR (400 MHz, CDCl$_3$): δ/ppm, 8.51 (d, 1H, J=0.8 Hz), 8.315 (dd, 1H, J=8.0, 1.2 Hz), 8.22 (s, 1H), 7.31-7.34 (m, 2H), 7.12 (s, 1H), 6.952 (d, 1H, J=8.4 Hz), 6.80 (s, 1H), 6.55 (s, 1H), 6.35 (s, 1H), 6.24 (t, 1H, J=5.2H z), 5.84 (s, 2H), 5.79 (s, 4H), 4.74 (s, 2H), 4.25 (s, 4H), 3.33-3.80 (m, 21H), 2.12-2.37 (m, 12H), 1.35-1.81 (m, 8H)

HRMS (ESI$^+$): Calcd. for [M+H]$^+$ 1271.29213; Found 1271.28895; Δ=0.00318.

The HPLC chromatogram (absorbance at 254 nm) is shown in FIG. 1. Analysis conditions were as follows: Using an ODS-C$_{18}$ column, the ratio of liquid A (0.1% TFA/H$_2$O): liquid B (0.1% TFA/CH$_3$CN) was linearly changed from 95:5 to 5:95 over a period of 1200 seconds, after which time set to a ratio of 5:95.

[Preparation of Measurement Sample and Measurement Method]

(1) Acquisition of Hydrolysate by Esterase Treatment

A 100 μL PBS solution containing Compound 14 (final concentration 80 μM), Pluronic F127 (0.2%), and Esterase *Pseudomonas fluorescens* (0.42 units/μL) (SIGMA) was prepared and hydrolysis reaction was carried out at 37° C. To follow the time course of the reaction, a part of the sample was taken during the reaction and the fluorescence intensity in 10 mM Ca$^{2+}$ buffer was measured with a spectrofluorophotometer (JASCO, FP-6500). When the fluorescence intensity ceased to change almost completely, the reaction was stopped to obtain a hydrolysate of Compound 14.

(2) Preparation of Ca$^{2+}$ Buffer

A free Ca$^{2+}$ concentration in a buffer containing 100 mM KCl and 30 mM 3-morpholinopropanesulfonic acid (MOPS) was adjusted using a Ca-ethylene glycol tetraacetic acid (EGTA) system (0-1 μM), a Ca-nitrilotriacetic acid (NTA) system (3.2 μM-794.3 μM), an unbuffered system (CaCl$_2$) (3.2 mM-10 mM). The adjustment of free Ca$^{2+}$ concentration in the Ca-EGTA system or in the Ca-NTA system was carried out using the following formula (1).

$$[Ca^{2+}]_0=([Ca^{2+}]+([L]_0+K_d)[Ca^{2+}])/(K_d+[Ca^{2+}])$$  Formula (1):

([Ca$^{2+}$]$_0$: calcium initial concentration, [Ca$^{2+}$]: free calcium concentration, [L]$_0$: chelator initial concentration, K$_d$: chelator dissociation constant)

(3) Cell Culture

HEK 293T cells (GenHunter) were cultured in Dulbecco's Modified Eagle's Medium (DMEM) (Wako) containing 10% FBS, 4 mM L-glutamine (Wako), and 1 mM sodium pyruvate (Wako) at 37° C. in an atmosphere of 5% CO$_2$. For nerve cells, a fetus was removed from Sprague-Dawley rat on day 21 of pregnancy under anesthesia, and the hippocampus immediately extracted from the fetal brain was digested with trypsin (Invitrogen) and DNase I (Sigma) to separate nerve cells. The nerve cells were cultured on a monolayer of glial cells in a Neurobasal A medium (Invitrogen) containing 2% B-27 supplement (Invitrogen), 1 mM sodium pyruvate (Wako), 1% glutamax (Invitrogen), 1% penicillin-streptomycin mixed solution (nacalai tesque) at 37° C. in an atmosphere of 5% CO$_2$.

(4) Preparation of pcDNA Halo-RimZF-CAAX vector

A DNA fragment encoding HaloTag was amplified by PCR using pFC14A (HaloTag 7) CMV Flexi vector (Promega) as a template. Also, by PCR using a plasmid pCI-neo RIM1α provided by Professor Yasuo Mori of Kyoto University as a template, the gene region encoding the Zinc-finger domain (56-228aa) (hereinafter referred to as "RimZF") of the mouse RIM1α gene was amplified.

Next, a DNA fragment encoding HaloTag and a DNA fragment encoding RimZF were fused by PCR. At this time, a DNA fragment expressing a fusion protein of HaloTag, RimZF, and CAAX motif was obtained by adding a DNA sequence encoding a CAAX motif of the KRas gene (KMSKDGKKKKKKSKTKC-VIM) to the primer. HindIII site and NotI site were added to this fragment and subcloned into the HindIII/NotI site of pcDNA 3.1(+) vector (Life Technologies) to obtain a desired vector pcDNA Halo-RimZF-CAAX.

(5) Preparation of Lentivirus

A DNA fragment obtained by fusing a sequence encoding a HaloTag protein in series on the C-terminal side of the DNA sequence encoding the vesicular membrane glutamine transporter (VGLUT1) was subcloned into a lentiviral vector (pLenti6PW) to prepare pLenti vglut1-chalo. The obtained pLenti vglut1-chalo was transfected into HEK 293T cells together with a helper plasmid (psPAX2, pMD2.G), cultured for 18 hours at 37° C. with a carbon dioxide concentration of 5%, then medium exchange was carried out, and the virus was recovered after culturing again at 37° C. for 24 and a half hours in an environment with 5% carbon dioxide concentration.

(6) Gene Transfer 350,000 HEK 293T cells per well were seeded in a 12-well plate (Thermo Fisher Scientific) coated with 0.01% collagen and 25 µg/ml poly-L-lysine (nacalai tesque) and after 5 hours, 1 µg of pcDNA Halo-RimZF-CAAX was transferred using Lipofectamine 2000 (Invitrogen). Nerve cells were infected on day 17 of culture and vglut1-chalo was transferred thereinto.

(7) Labeling of Cells

HEK 293T cells were seeded in metal rings on a cover glass coated with 0.01% collagen and 25 µg/ml poly-L-lysine (nacalai tesque) 16 hours after gene transfer so that the number of cells per ring was 40,000 and cultured at 37° C. and a carbon dioxide concentration of 5%. Three and a half hours later, the extracellular fluid was replaced with Ringer's solution (5 mM HEPES, 150 mM NaCl, 4 mM KCl, 2 mM $CaCl_2$, 1 mM $MgCl_2$, 0.1% glucose, pH 7.2) containing a $Ca^{2+}$ probe (compound 14 or Calcium Green, AM (Invitrogen)) or a fluorescent ligand (halo TMR, halo Oregon) (final concentration 5 µM) and 0.02% Pluronic F127 and left to stand at room temperature for 30 minutes while being shielded from light. The cells labeled with compound 14 and the fluorescent ligand was then exchanged with serum-free DMEM, removal of probes that were liberated at 5% carbon dioxide concentration and 37° C. was carried out for 30 minutes, and the extracellular solution was exchanged again with Ringer's solution. The cells stained with Calcium Green, AM were observed with fluorescence immediately after washing with Ringer's solution. The nerve cells were labeled with Ringer's solution containing compound 14 (final concentration 5 µM) for 15 minutes on day 9 after virus infection.

(8) In Situ Calibration

The labeled HEK 293T/Halo-RimZF-CAAX was immobilized with 4% PFA/PBS for 10 minutes, subjected to membrane permeabilization with 20 µM digitonin, and a change in fluorescence when the $Ca^{2+}$ concentration of the extracellular solution was changed was measured.

(9) $Ca^{2+}$ Imaging

Fluorescence images were acquired using an inverted microscope (IX-71, Olympus), an EM-CCD camera (Andor, iXon), an objective lens (iXonpus was measured through an objective lens, Olympus), and a filter set for RFP. The HEK 293T cells were stimulated with ionomycin (10 µM), and images were acquired over time at intervals of 5 seconds. The nerve cells were subjected to electrical stimulation (7V, 100 ms interval, 10 times) 5 times, and images were acquired at 50 Hz.

Example 2

Evaluation of Chemical Characteristics of Compound 14

In order to evaluate the chemical characteristics of the synthesized Compound 14, a hydrolysate was obtained by esterase treatment according to the above method, and the fluorescence intensity in a buffer in which the $Ca^{2+}$ concentration was adjusted was measured with a spectrofluorophotometer.

Figure 2:
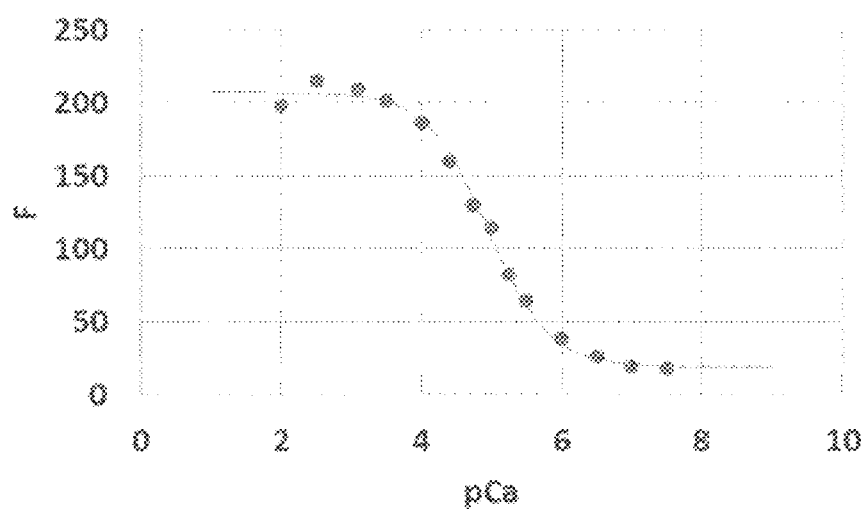
FIG. 2 shows in vitro titration of hCGapt3.

As a result, the fluorescence intensity of the probe bound to $Ca^{2+}$ was about 11 times larger (Fmax/Fmin=10.8) than that of the unbound probe, and the dissociation constant (Kd) was 11.1 µM (FIG. 2). In FIG. 2, the black circles (●) indicate each data point, which showed a fit curve that is a curved line.

Example 3

Evaluation of Localization and $Ca^{2+}$ Response Characteristics in HEK 293T Cells Staining with a fluorescent probe was performed using HEK 293T cells expressing a HaloTag protein on the cell membrane by introducing pcDNA Halo-RimZF CAAX gene (hereinafter referred to as HEK 293T/Halo-RimZF-CAAX). With Calcium Green, AM, the cytoplasm of all cells in the visual field was stained regardless of expression of the HaloTag protein (FIG. 3A). On the other hand, with Compound 14, unlike conventional probes, fluorescence localized on the cell membrane on which the HaloTag protein is expressed was observed (FIG. 3B). The expression site of the HaloTag protein was identified by staining with a HaloTag ligand.

Next, $Ca^{2+}$ response characteristics of the labeled probe were evaluated by in situ calibration. As a result, it was found that Fmax/Fmin was 4.7 and Kd was 6.4 µM (FIG. 4). In FIG. 4B, the black circles (●) indicate each data point, which showed a fit curve that is a curved line.

In addition, ionomycin was added to a probe-labeled HEK 293T/Halo-RimZF-CAAX in order to see the response characteristics to the $Ca^{2+}$ signal induced by the ionophore, and then changes with time of the fluorescence intensity were measured (FIG. 5). FIG. 5A shows a label of HEK 293T/Halo-RimZF-CAAX, and FIG. 5B shows a change in fluorescence intensity due to ionomycin stimulation. In FIG. 5B, the point of stimulation is indicated by black arrows.

As shown in FIG. 5B, the addition of ionomycin increased the fluorescence intensity and the local $Ca^{2+}$ signal on the cell membrane was detected.

Example 4

Evaluation of Response Characteristics to $Ca^{2+}$ Signal by Electrical Stimulation Using Nerve Cells Rat hippocampus-derived nerve cells expressing a fusion protein (dynein-Halo) of dynein light chain protein showing localization at the synapse and HaloTag were stained with a probe, and electrical stimulation was applied 10 times at 100 Hz to induce successive action potentials, and then a $Ca^{2+}$ signal change corresponding to the stimulus was observed (FIG. 6).

Here, FIG. 6A shows the rat hippocampus-derived nerve cells/vglut1-chalo, and FIG. 6B shows the change in fluorescence intensity (100 Hz, 10 times) when subjected to electrical stimulation.

What is claimed is:

1. A compound represented by the following general formula (I) or a salt thereof:

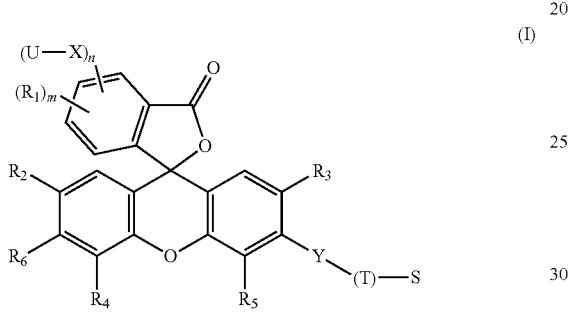

(wherein,
$R_1$ at each occurrence represents a hydrogen atom or a monovalent substituent on the benzene ring, and when more than one monovalent substituent are present, they may be the same or different, and said monovalent substituent is a halogen or an alkyl group which may be substituted;

$R_2$ and $R_3$, each independently, represent a hydrogen atom, an alkyl group having 1 to 6 carbon atoms or a halogen atom;

$R_4$ and $R_5$, each independently, represent a hydrogen atom, an alkyl group having 1 to 6 carbon atoms or a halogen atom;

$R_6$ represents an acetoxy group, an acetoxymethoxy group, or a hydroxyl group;

X is selected from a carbonyl group, an amide group or an alkylcarbonyl group;

U represents a group capable of capturing calcium ions after hydrolysis, wherein said group capable of capturing calcium ions after hydrolysis is selected from the group consisting of an ester compound of an aminophenol triacetic acid derivative and an ester compound of 1,2-bis(o-aminophenoxide)ethane-N, N,N',N'-tetraacetic acid derivative;

Y is azetidine;

T, if present, represents a cross-linking group, and said cross-linking group is a carbonyl group;

S represents a label site, and said label site is 2-(2-((6-chlorohexyl)oxy)ethoxy)ethaneamino group;

m is an integer of 1 to 3, and n is an integer of 1 to 3, with the proviso that m+n=4).

2. The compound according to claim 1 or a salt thereof, wherein X is an amide group.

3. A compound represented by the following formula or a salt

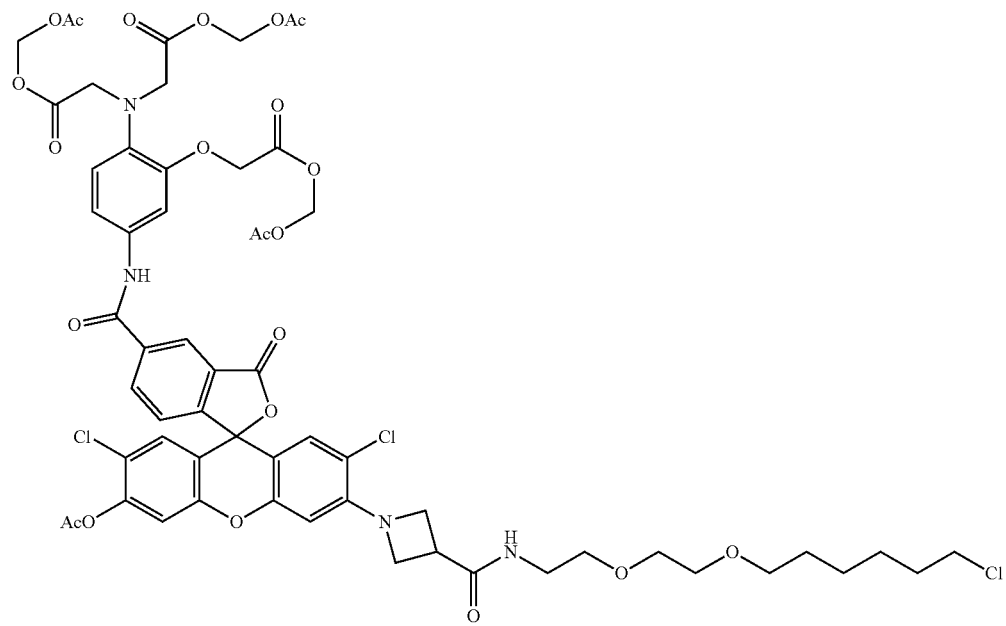 [SMILES: CC(=O)OCOC(=O)COc1cc(NC(=O)c2ccc3c(c2)C(=O)OC32c3cc(Cl)c(OC(C)=O)cc3Oc3cc(N4CC(C(=O)NCCOCCOCCCCCCCl)C4)c(Cl)cc32)ccc1N(CC(=O)OCOC(C)=O)CC(=O)OCOC(C)=O]

thereof.

4. A fluorescent probe comprising the compound according to claim 1 or a salt thereof.

5. A method for detecting intracellular calcium ions, comprising:
(a) introducing the compound according to claim 1 or a salt thereof into a cell, and (b) measuring the fluorescence emitted by the compound or a salt thereof in the cell.

* * * * *